(12) United States Patent
Ooshima et al.

(10) Patent No.: US 9,939,508 B2
(45) Date of Patent: Apr. 10, 2018

(54) MEDICAL IMAGE PROCESSING APPARATUS, MAGNETIC RESONANCE IMAGING APPARATUS, MEDICAL IMAGE PROCESSING METHOD AND MAGNETIC RESONANCE IMAGING METHOD

(71) Applicant: TOSHIBA MEDICAL SYSTEMS CORPORATION, Otawara-shi, Tochigi (JP)

(72) Inventors: Kiyomi Ooshima, Tochigi (JP); Tsutomu Igarashi, Tochigi (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 718 days.

(21) Appl. No.: 14/546,516

(22) Filed: Nov. 18, 2014

(65) Prior Publication Data

US 2015/0070016 A1    Mar. 12, 2015

Related U.S. Application Data

(63) Continuation of application No. PCT/JP2013/066073, filed on Jun. 11, 2013.

(30) Foreign Application Priority Data

Jun. 20, 2012 (JP) ................. 2012-139224

(51) Int. Cl.
*G01R 33/56* (2006.01)
*G01R 33/28* (2006.01)
(Continued)

(52) U.S. Cl.
CPC ........ *G01R 33/5608* (2013.01); *A61B 5/0035* (2013.01); *A61B 5/7425* (2013.01);
(Continued)

(58) Field of Classification Search
CPC . G06F 19/321; G01R 33/5608; G01R 33/283; G01R 33/4835; G01R 33/543;
(Continued)

(56) References Cited

U.S. PATENT DOCUMENTS 5,987,345 A * 11/1999 Engelmann ........... G06F 19/321
128/920
7,630,531 B2 * 12/2009 Chui .................... G06F 19/321
382/128

(Continued)

FOREIGN PATENT DOCUMENTS

JP    1996-294485    11/1996
JP    2002-301065    10/2002
(Continued)

OTHER PUBLICATIONS

Machine translation of Nemoto et al. (JP 2002-301,065 A). Pub Date Oct. 15, 2002.*
(Continued)

*Primary Examiner* — Rodney Bonnette
(74) *Attorney, Agent, or Firm* — Nixon & Vanderhye P.C.

(57) ABSTRACT

A medical image processing apparatus includes an image acquisition part and a display processing part. The image acquisition part is configured to acquire plural series, each having frames of medical image data corresponding to at least one of slice positions and time phases. The display processing part is configured to perform display processing to display image data in a region of interest of at least one frame of first medical image data belonging to a first series out of the plural series. The image data in the region of interest are overlapped with a region of at least one frame of second medical image data belonging to another series. The region of the at least one frame of the second medical image data is different from a region corresponding to the region the interest.

16 Claims, 5 Drawing Sheets

(51) Int. Cl.
*G01R 33/483* (2006.01)
*G01R 33/54* (2006.01)
*G01R 33/563* (2006.01)
*G06F 19/00* (2011.01)
*A61B 5/00* (2006.01)
*A61B 6/00* (2006.01)
*A61B 5/055* (2006.01)
*A61B 6/03* (2006.01)

(52) U.S. Cl.
CPC .............. *A61B 6/463* (2013.01); *A61B 6/469* (2013.01); *A61B 6/5235* (2013.01); *A61B 6/5247* (2013.01); *G01R 33/283* (2013.01); *G01R 33/4835* (2013.01); *G01R 33/543* (2013.01); *G01R 33/56308* (2013.01); *G06F 19/321* (2013.01); *A61B 5/055* (2013.01); *A61B 6/032* (2013.01); *A61B 6/037* (2013.01); *A61B 6/486* (2013.01)

(58) Field of Classification Search
CPC ............ G01R 33/56308; A61B 5/0035; A61B 5/7425; A61B 5/055; A61B 6/463; A61B 6/469; A61B 6/5235; A61B 6/5247; A61B 6/032; A61B 6/037; A61B 6/486
See application file for complete search history.

(56) References Cited

U.S. PATENT DOCUMENTS

| | | | |
|---|---|---|---|
| 8,355,775 B2 | 1/2013 | Oshiki et al. | |
| 9,595,088 B2 * | 3/2017 | Mohr | G06T 5/50 |
| 2005/0111757 A1 * | 5/2005 | Brackett | A61B 6/463 382/294 |
| 2009/0087047 A1 * | 4/2009 | Moriya | A61B 5/7425 382/128 |
| 2010/0106002 A1 | 4/2010 | Sugiyama et al. | |

FOREIGN PATENT DOCUMENTS

| | | |
|---|---|---|
| JP | 2007-029248 | 2/2007 |
| JP | 2007-275216 | 10/2007 |
| JP | 2010-119831 | 6/2010 |

OTHER PUBLICATIONS

Machine translation of Miyazaki et al. (JP 2007-029,248 A). Pub Date Feb. 8, 2007.*
Machine translation of Oishi et al. (JP 08-294,485 A). Pub Date Nov. 12, 1996.*
Machine translation of Moriya et al. (JP 2007-275,216 A). Pub Date Oct. 25, 2007.*
Office Action dated Apr. 3, 2015 CN Patent Application No. 201380000855.8.
Notification of Transmittal of Translation of the International Preliminary Report on Patentability in PCT/JP2013/066073 dated Dec. 31, 2014.
Office Action dated Jan. 27, 2016 in CN Patent Application No. 201380000855.8.
Chinese final rejection dated Aug. 1, 2016 in CN Patent Application No. 201380000855.8.
Japanese office action dated Mar. 28, 2017 in Patent Application No. JP 2013-122645.
Chinese retrial notice issued May 2, 2017 in Patent Application No. 201380000855.8.
International Search Report for PCT/JP2013/066073 dated Jul. 9, 2013.

* cited by examiner

MEDICAL IMAGE PROCESSING APPARATUS, MAGNETIC RESONANCE IMAGING APPARATUS, MEDICAL IMAGE PROCESSING METHOD AND MAGNETIC RESONANCE IMAGING METHOD

CROSS REFERENCES TO RELATED APPLICATIONS

This is a continuation of Application PCT/JP2013/66073, filed Jun. 11, 2013.

This application is based upon and claims the benefit of priority from Japanese Patent Application No. 2012-139224, filed Jun. 20, 2012; the entire contents of which are incorporated herein by reference.

FIELD

Embodiments described herein relate generally to a medical image processing apparatus, an MRI (magnetic resonance imaging) apparatus, a medical image processing method and a magnetic resonance imaging method.

BACKGROUND

Medical images, such as magnetic resonance (MR) images, acquired with a diagnostic imaging apparatus, such as an MRI apparatus, are used as targets of comparative reading with a viewer. For example, multiple medical images of a lesion area, which has been acquired from a same object before and after an operation, can be displayed in parallel. For this reason, a user can observe a change in a region of interest (ROI) before and after an operation.

PRIOR TECHNICAL LITERATURE

[Patent literature 1] JPA H08-294485

When multi-slice images are acquired repeatedly, the data size becomes huge. For this reason, high-capacity storage and data processing for data having a large size are needed for comparative reading of medical images.

Accordingly, an object of the present invention is to provide a medical image processing apparatus, a magnetic resonance imaging apparatus, a medical image processing method and a magnetic resonance imaging method which can display medical images for a comparison interpretation more simply based on medical image data having less data size.

DETAILED DESCRIPTION

Figure 1:
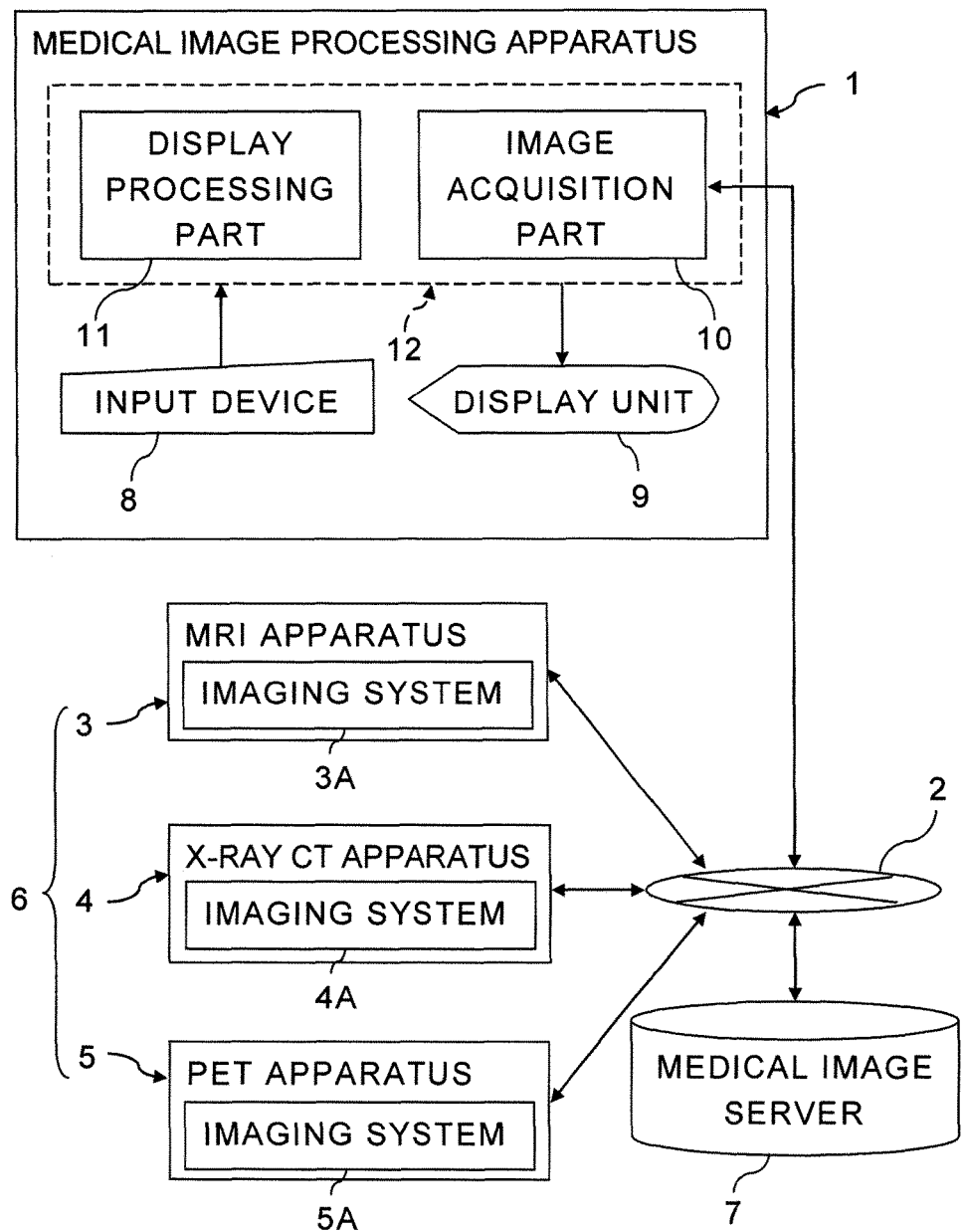
FIG. 1 is a configuration diagram of the whole system including a medical image processing apparatus according to an embodiment of the present invention.

In general, according to one embodiment, a medical image processing apparatus includes an image acquisition part and a display processing part. The image acquisition part is configured to acquire plural series, each consisting of frames of medical image data corresponding to at least one of slice positions and time phases. The display processing part is configured to perform display processing to display image data in a region of interest of at least one frame of first medical image data belonging to a first series out of the plural series. The image data in the region of interest are overlapped with a region of at least one frame of second medical image data belonging to another series. The region of the at least one frame of the second medical image data is different from a region corresponding to the region of interest.

Further, according to another embodiment, magnetic resonance imaging apparatus includes an imaging system and a display processing part. The imaging system is configured to acquire plural series, each consisting of frames of medical image data corresponding to at least one of slice positions and time phases, by magnetic resonance imaging. The display processing part is configured to perform display processing to display image data in a region of interest of at least one frame of first medical image data belonging to a first series out of the plural series. The image data in the region of interest are overlapped with a region of at least one frame of second medical image data belonging to another series. The region of the at least one frame of the second medical image data is different from a region corresponding to the region of interest.

Further, according to another embodiment, a medical image processing method includes acquiring plural series, each consisting of frames of medical image data corresponding to at least one of slice positions and time phases; and performing display processing to display image data in a region of interest of at least one frame of first medical image data belonging to a first series out of the plural series. The image data in the region of interest are overlapped with a region of at least one frame of second medical image data belonging to another series. The region of the at least one frame of the second medical image data is different from a region corresponding to the region of interest.

Further, according to another embodiment, a magnetic resonance imaging method includes acquiring plural series, each consisting of frames of medical image data corresponding to at least one of slice positions and time phases, by magnetic resonance imaging; and performing display processing to display image data in a region of interest of at least one frame of first medical image data belonging to a first series out of the plural series. The image data in the region of interest are overlapped with a region of at least one frame of second medical image data belonging to another series. The region of the at least one frame of the second medical image data is different from a region corresponding to the region of interest.

A medical image processing apparatus, a magnetic resonance imaging apparatus, a medical image processing method and a magnetic resonance imaging method according to embodiments of the present invention will be described with reference to the accompanying drawings.

FIG. 1 is a configuration diagram of the whole system including a medical image processing apparatus according to an embodiment of the present invention.

A medical image processing apparatus 1 is connected with image diagnostic apparatuses 6 such as an MRI apparatus 3, an X-ray CT (computed tomography) apparatus 4, and a PET (positron emission computed tomography) apparatus 5 in addition to a medical image server 7 through a network 2.

The medical image processing apparatus 1 can be configured by a large-scale computer, such as a workstation, reading a medical image processing program. However, a circuit may be used to configure the medical image processing apparatus 1. The medical image processing apparatus 1 may be built in an image diagnostic apparatus 6. In that case, the medical image processing program is installed in a computer which constitutes the image diagnostic apparatus 6.

The medical image server 7 is a storage unit, such as a picture archiving and communication system (PACS), for storing medical image data. The medical image server 7 may have a simple image processing function and a function as an image viewer. Therefore, the function as the medical image processing apparatus 1 may be also provided in the medical image server 7.

Each image diagnostic apparatus 6 is an apparatus to acquire medical image data of an object. In case of an MRI apparatus 3, an imaging system 3A to acquire MR image data by MR imaging of an object is included. In MR imaging, MR signals are acquired by applying radio frequency (RF) magnetic fields and gradient magnetic fields to an object under a static magnetic field. Then, MR image data is generated by image reconstruction processing of MR signals.

Medical image data acquired by an image diagnostic apparatus 6, such as the MRI apparatus 3, can be transferred to and stored in the medical image server 7. When multi-slice imaging is performed in an image diagnostic apparatus 6, multi-slice image data for plural frames are acquired as medical image data. The medical image data, corresponding to multiple slices, which have been acquired by imaging once are classified as frames of image data belonging to one series.

Therefore, when multiple examinations for a same part of a same object have been performed on different dates and times, multi-slice image data sets or single slice image data sets, of the same imaging part, belonging to multiple series are acquired as medical image data.

Moreover, when multi-slice image data or single slice image data are dynamically acquired as moving images or a moving image, frames of image data corresponding to time phases are classified as frames of medical image data belonging to one series. That is, one series is consisted of multiple frames of medical image data corresponding to at least one of multiple slice positions and multiple time phases.

For example, the MRI apparatus 3 performs MR imaging at different timing by the imaging system 3A. Thereby, multiple frames of MR image data corresponding to positions, which can be regarded as same, are acquired as medical image data from an object.

More in particular, the imaging system 3A acquires multiple series by MR imaging. Each series consists of multiple frames of medical image data corresponding to at least one of multiple slice positions and multiple time phases.

Then, transferring and storing frames of medical image data, corresponding to positions, which can be considered to be same, of a same object, to and in the medical image server 7 allow comparative reading for follow-up or the like of the object before and after an operation.

Moreover, not only frames of medical image data before and after an operation but frames of medical image data acquired under imaging conditions for obtaining different contrasts may be a target of comparative reading. Specific examples include frames of MR image data, such as longitudinal relaxation (T1) weighted image data and transverse relaxation (T2) weighted image data acquired under different imaging conditions by the MRI apparatus 3.

Further, not only frames of medical image data of a same object but frames of medical image data at corresponding positions of different objects may be a target of comparative reading. Furthermore, not only frames of medical image data acquired by a same modality but frames of medical image data acquired by different modalities may be a target of comparative reading.

By the medical image processing apparatus 1, comparative reading of frames of medical image data corresponding to approximately same positions of a same object can be performed. For that purpose, the medical image processing apparatus 1 has an input device 8, a display unit 9, an image acquisition part 10 and a display processing part 11. When the medical image processing apparatus 1 is configured by installing a medical image processing program in a computer, the medical image processing program stored in a storage unit functions an operation unit 12 of the computer as the image acquisition part 10 and the display processing part 11.

The medical image processing apparatus 1 can have functions to perform various image processing of medical image data. In other words, functions for comparative reading can be provided to the medical image processing apparatus 1 having functions to perform various image processing.

The image acquisition part 10 has a function to acquire multiple frames of medical image data for comparative reading from an arbitrary medical system such as the medical image server 7 or the image diagnostic apparatus 6. The frames of medical image data acquired by the image acquisition part 10 are data acquired from a same object or different objects at different timings and correspond to positions which can be regarded as the same. That is, the image acquisition part 10 has a function to acquire multiple series, each consisting of frames of medical image data corresponding to at least one of multiple slice positions and multiple time phases.

When the medical image processing apparatus 1 is built in the image diagnostic apparatus 6, the image acquisition part 10 is configured to acquire medical image data from an imaging system 3A, 4A or 5A of a same or another image diagnostic apparatus 6. The image acquisition part 10 may acquire multiple frames of medical image data acquired by different modalities.

The display processing part 11 has a function to perform display processing for displaying medical image data in a ROI of at least one frame of medical image data out of frames of medical image data, acquired by the image acquisition part 10, simultaneously with another frame of medical image data. In addition, the display processing part 11 has a function to display medical image data, after display processing, on the display unit 9. Examples of a method for simultaneously displaying medical image data in a ROI with another frame of medical image data include a method for displaying medical image data in a ROI superimposed at the corresponding position of another frame of medical image data and a method for parallel-displaying medical image data in a ROI at an arbitrary position such as a neighborhood of the corresponding position of another frame of medical image data.

When medical image data in a ROI is superimposed on the corresponding position of another frame of medical image data, coordinate information of the medical image data in a body coordinate system fixed to an object is necessary. Accordingly, the display processing part 11 is configured to refer to coordinate information, in a body coordinate system, attached to medical image data as incidental information or related to medical image data, and to perform necessary coordinate conversion processing, extraction processing of a region corresponding to a ROI and composition processing of image data.

A ROI to be extracted from medical image data and superimposed with medical image data can be previously set on a desired frame of medical image data using an arbitrary medical system such as the image diagnostic apparatus 6 or an image server. A ROI can be also set to a desired frame of medical image data latterly by operating the input device 8 in the medical image processing apparatus 1. An annotation can also be given to the set ROI.

When an examination to acquire multi-slice image data from an object has been performed repeatedly, frames of medical image data corresponding to multiple different series and multiple different slice positions are acquired by the image acquisition part 10. In this case, each series corresponds to a time and date of an examination, and the multiple slice positions can be regarded as same between the multiple series.

On the other hand, when a dynamic imaging has been performed repeatedly to a same single slice or same multi slices, frames of medical image data corresponding to multiple different series and multiple different time phases are acquired by the image acquisition part 10. In this case, each series also corresponds to a time and date of an examination, and a single slice position or multiple slice positions can be regarded as same between the multiple series.

When frames of medical image data belonging to multiple series have been acquired, display processing for displaying medical image data, in a ROI of at least one frame of the medical image data belonging to at least one series out of the multiple series, and medical image data belonging to another series at the same time can be performed. That is, medical image data outside a ROI can be common between frames of medical image data belonging to different series.

Furthermore, when multi-slice image data have been acquired for each series, display processing for displaying pieces of medical image data, inside respective ROIs of frames of medical image data which correspond to multiple slice positions and belong to at least one series, with superimposing the pieces of the medical image data with corresponding positions of frames of medical image data which correspond to the multiple slice positions and belong to another series or other multi series. That is, pieces of medical image data outside ROIs which are set for respective slice positions can be common between multi-slice image data sets belonging to different series.

Figure 2:
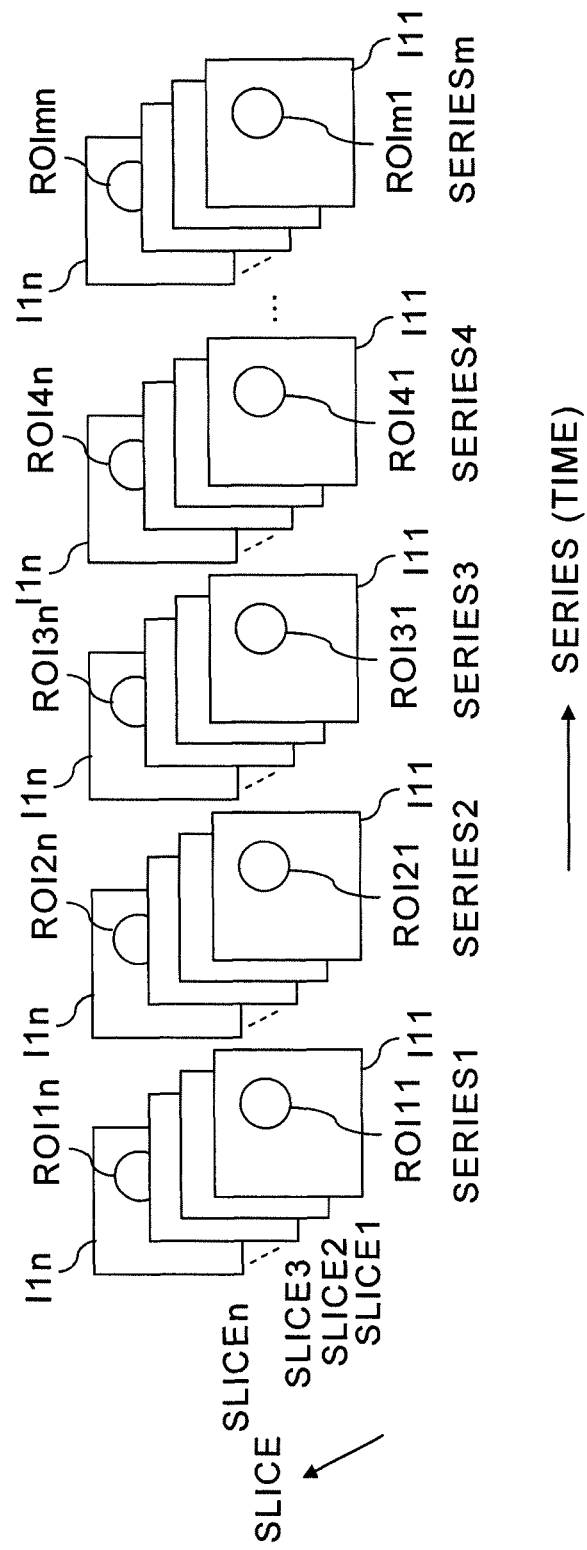
FIG. 2 is a view for explaining the first example of display processing performed in the display processing part shown in FIG. 1.

FIG. 2 is a view for explaining the first example of display processing performed in the display processing part 11 shown in FIG. 1.

In FIG. 2, the horizontal axis represents the series axis direction which corresponds to the time axis direction. FIG. 2 shows an example case of display processing for respectively superimposing and displaying pieces of medical image data (ROI21, . . . , ROImn) in respective ROIs on frames of medical image data, at multiple slice positions (slice1, slice2, slice3, . . . , slicen), which belong to multiple series (series2, series3, series4, . . . seriesm) excluding one reference series (series1), on corresponding positions on frames of medical image data (I11, I12, I13, . . . , I1n), at the multiple slice positions (slice1, slice2, slice3, . . . , slicen), belongs to the reference series (series1). In other words, the pieces of the medical image data (I11, I12, I13, . . . , I1n) belonging to a certain series (series1) serving as a reference are used as pieces of medical image data outside the ROIs.

The reference medical image data can be medical image data acquired in arbitrary timing, like medical image data before an operation or medical image data after an operation. Therefore, not only multi-slice data acquired at the earliest period as shown in FIG. 2 but multi-slice image data acquired at arbitrary timing, such as the latest period, may be used as reference medical image data which are commonly used.

The frames of medical image data obtained by composing pieces of medical image data inside ROIs with pieces of medical image data outside the ROIs can be displayed in parallel or with switching them on the display 9. When frames of medical image data are switched to be displayed, the switching display can be performed in a predetermined order, like a work to turn pages. The function to switch and display frames of medical image data in a predetermined order is also called a browse function.

For example, the display processing part 11 can respond to a switching instruction of an image, which should be displayed, input from the input device 8 and perform display processing for switching and displaying frames of medical image data in a slice direction. Alternatively, the display processing part 11 may perform display processing for switching and displaying frames of medical image data in a series direction, in response to a switching instruction of an image, which should be displayed, input from the input device 8. That is, frames of composite image data can be switched to be displayed, like turning pages in a slice or series direction.

When frames of medical image data are switched in a slice direction, frames of composite image data, inside and outside ROIs, at respective slice positions are sequentially switched to be displayed, in the condition that a series to be a display target has been specified. Therefore, a spatial observation of an imaging part at a time point of a certain examination becomes possible.

On the other hand, when frames of medical image data are switched in a series direction, frames of composite image data, inside and outside ROIs, in respective series are sequentially switched to be displayed, in the condition that a slice position to be a display target has been specified. Therefore, a follow-up observation inside a ROI at a certain slice position becomes possible.

Although FIG. 2 shows the example of setting a single ROI per one frame, similar display processing can be also performed to frames of medical image data, each having multiple ROIs. Moreover, in a case where frames of medical image data, which are a target of comparative reading, correspond to multiple time phases, the frames of the medical image data can be displayed, in parallel or with switching them, not in a slice direction but in the time phase direction.

Figure 3:
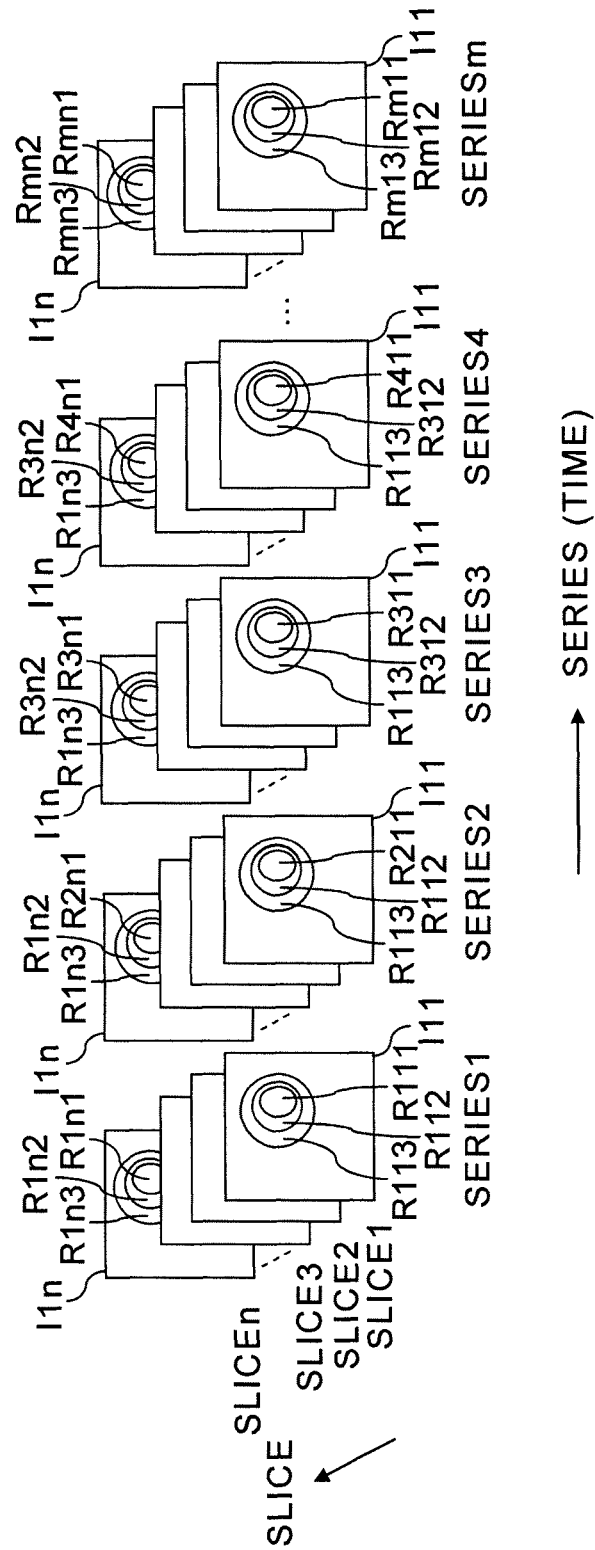
FIG. 3 is a view for explaining the second example of display processing performed in the display processing part shown in FIG. 1.

FIG. 3 is a view for explaining the second example of display processing performed in the display processing part 11 shown in FIG. 1.

In FIG. 3, the horizontal axis represents the series axis direction and the time axis direction. As shown in FIG. 3, display processing for simultaneously displaying pieces of medical image data inside multiple ROIs (R111, . . . , Rmn3) on at least one frame of medical image data, together with another frame or other frames of medical image data, can be performed. FIG. 3 shows an example that pieces of medical image data (I11, I12, I13, . . . , I1n), outside ROIs (R111, . . . , Rmn3), at slice positions (slice1 slice2, slice3, . . . , slicen) are in common among multiple series (series1, series2, series3, . . . , seriesm), similarly to the example shown in FIG. 2

However, when multiple ROIs are on each frame, a piece or pieces of medical image data in a part of the ROIs may be also in common among multiple series. In this case, when frames of medical image data are switched in a series direction and displayed on the display 9, display frequencies of pieces of medical image data in the multiple ROIs differ between the multiple ROIs. Therefore, display processing is performed in the display processing part 11 so that frames of medical image data are switched and displayed in a series direction with update frequencies different between the ROIs.

For example, multiple ROIs (R111, . . . , Rmn3) according to distances from a portion focused as a lesion part can be set as shown in FIG. 3. Then, a piece of medical image data in a ROI, whose distance from the focused portion is longer, can be in common among more series (series1, series2, series3, . . . , seriesm). Thereby, a time-series medical image group can be displayed on the display 9 with switching them so that a piece of medical image data in a part closer to a focused part is updated more frequently.

In addition, the background region outside ROIs may be also in common between the series. This is the same in case where a single ROI is set per one frame. In this case, a time-series medical image group can be displayed on the display 9 with switching them so that the inside of the ROI is updated more frequently than the outside of the ROI.

When frames of medical image data to be a target of comparative reading correspond to multiple time phases, the frames of the medical image data can be displayed in parallel or with switching them, not in a slice direction but in the time phase direction, also in the second example, similarly to the first example shown in FIG. 2.

Figure 4:
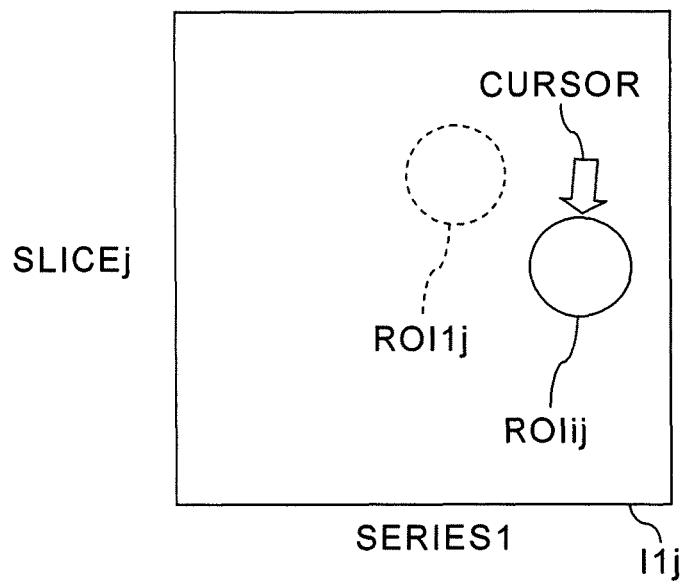
FIG. 4 is a view for explaining the third example of display processing performed in the display processing part shown in FIG. 1.

FIG. 4 is a view for explaining the third example of display processing performed in the display processing part 11 shown in FIG. 1.

FIG. 4 shows an example case of displaying an image in a ROI (ROIij) set on an image at the j-th slice position (slicej) in the i-th series (seriesi), simultaneously with a reference image. When the first series (series1) is a reference, the image I1j corresponding to the j-th slice position (slicej) and the first series (series1) is displayed.

Then, the image in the ROI (ROW) set on the image at the j-th slice position (slicej) in the i-th series (seriesi) can be displayed at a position according to a position of a cursor such as a neighborhood of the cursor. That is, the image data in the ROI (ROIij) used as a composition target can be composed at a position different from the corresponding position on image data used as a composition destination, intentionally. In this case, both the image in the ROI (ROI1j), shown by the dotted frame, set for the image I1j corresponding to the j-th slice position (slicej) in the first series (series1) and the image in the ROI (ROIij) set on the image at the j-th slice position (slicej) in the i-th series (seriesi) are displayed on the image I1j when the cursor is put on a suitable position.

For this reason, a user can compare images in ROIs, whose slice positions are regarded as same, belonging to different plural series, with each other, on a same image. In this case, a distance between parts to be compared becomes shorter compared to a case of comparative reading by displaying two frames of images in parallel. Therefore, a moving distance of visual line becomes shorter and comparative reading becomes easier.

As shown in FIG. 4, display processing can be performed so that image data in a ROI of at least one frame of the first medical image data belonging to the first series out of multiple series are displayed and superimposed at a region, different from the region corresponding to the ROI, of at least one frame of the second medical image data belonging to another series.

In the example shown in FIG. 4, display processing has been performed so that image data in a ROI are displayed and superimposed at a position, designated by an operation of the input device 8, of the second medical image data. However, display processing may be performed so that image data in a ROI are displayed and superimposed within a predetermined range, from the region corresponding to the ROI, of the second medical image data. In this case, the image data in the ROI can be automatically displayed and superimposed near the second medical image data or the like.

When image data in a ROI of the first medical image data are displayed and superimposed at a region, different from the region corresponding to the ROI, of the second medical image data, frames of the second medical image data can be displayed in parallel or with switching them. For example, the display processing part 11 can perform display processing so that frames of the second medical image data are switched in a slice direction or the time phase direction to be displayed, in response to a switching instruction of a display target image, input from the input device 8.

In that case, the image data in the ROI can be switched and displayed according to a slice position or a time phase of a frame of the second medical image data. Furthermore, a switching frequency of the image data in the ROI may be changed from that of the second medical image data.

Figure 5:
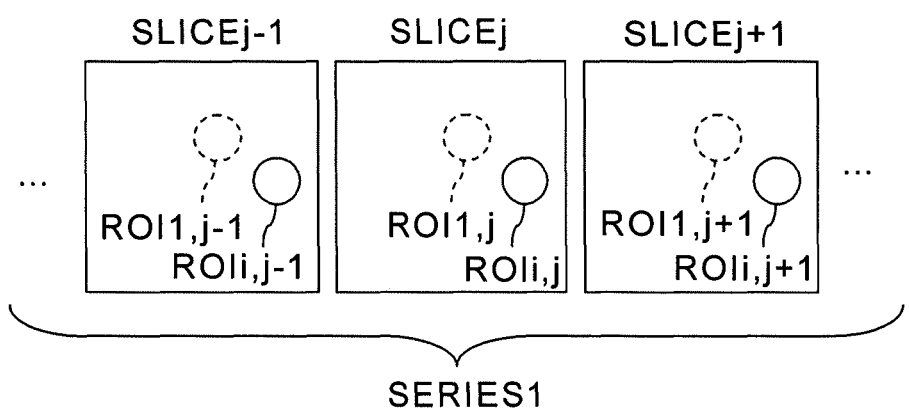
FIG. 5 is a view for explaining the fourth example of display processing performed in the display processing part shown in FIG. 1.

FIG. 5 is a view for explaining the fourth example of display processing performed in the display processing part 11 shown in FIG. 1.

FIG. 5 shows an example of displaying frames of the second medical image data, at different slice positions ( . . . , slicej−1, slicej, slicej+1, . . . ), belonging to the first same series (series1), in parallel in a slice direction. Note that, frames of the second medical image data, at different time phases, belonging to a same series can be also displayed in parallel in the time phase direction, in a similar way.

As shown in FIG. 5, frames of the second medical image data belonging to a series other than the first series as the i-th series can be displayed in parallel in a slice direction or the time phase direction. In that case, pieces of image data ( . . . , (ROIi, j−1), (ROIi, j), (ROE, j+1), . . . ) in ROIs of frames of the first medical image data at slice positions or time phases corresponding to those of the frames of the second medical image data can be respectively superimposed and displayed at regions different from the regions ( . . . , (ROI1, j−1), (ROI1, j), (ROI1, j+1), . . . ), corresponding to the ROIs, of the corresponding frames of the second medical image data. That is, a slice position or a time phase of image data in a ROI of the first medical image data can correspond to that of the second medical image data.

Note that, multiple frames of composite image data as shown in FIG. 5 may be switched to be displayed instead of a parallel display, as mentioned above.

Figure 6:
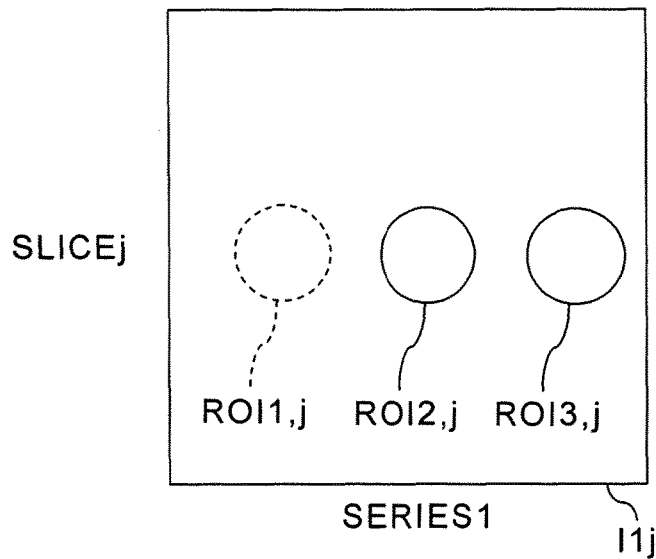
FIG. 6 is a view for explaining the fifth example of display processing performed in the display processing part shown in FIG. 1.

FIG. 6 is a view for explaining the fifth example of display processing performed in the display processing part 11 shown in FIG. 1.

When a ROI does not lie on the corresponding position on a frame of the second medical image data to be superimposed with the image data in the ROI, pieces of image data in some ROIs can be superimposed on a frame of the second medical image data.

Accordingly, image data in a ROI on at least one frame of the first medical image data belonging to the first series out of multiple series and additional image data in the corresponding ROI on at least one frame of the third medical image data belonging to the third series can be superimposed and displayed on a frame of the second medical image data so that the image data of the third medical image data lie on a position different from each of the corresponding region of the second medical image data and the position of the image data in the ROI on the first medical image data, as shown in FIG. 6.

In the example shown in FIG. 6, image data (ROI2,j) in the ROI of the first medical image data have been superimposed and displayed at a position different from the region (ROI1, j) of the second medical image data (I1j) at the slice j which belongs to the first series. Furthermore, image data (ROI3, j) in the ROI, of the third medical image data, corresponding to the ROI of the first medical image data have been superimposed and displayed at a position different from each of the region (ROI1, j) of the second medical image data (I1j) and a display region of the image data (ROI2, j) in the ROI of the first medical image data.

Such superimposing and displaying plural pieces of image data in ROIs on a frame of the second medical image data allows comparative reading of three or more images only by moving a visual line in a small area. Of course, a slice axis may be changed into the time phase axis.

Note that, an image in a ROI to be a composite target can be displayed in the optimal size according to a spatial resolution. When a spatial resolution is high, an image in a ROI to be a composite target may be enlarged to be displayed. That is, the display processing part 11 can perform enlargement processing or reduction processing of an image in a ROI to be a composite target, according to a spatial resolution of the image data in the ROI, so that the image in the ROI to be the composite target is not displayed extremely rough.

As mentioned above, frames of medical image data belonging to multiple series may be acquired by not only a same kind of modality but also different kinds of modality. Therefore, in the display processing part 11, display processing is performed so that image data in a ROI of the first medical image data are superimposed and displayed on the second image data which have been acquired by a same or different kind of modality.

When image data in a ROI of the first medical image data are superimposed and displayed on the second medical image data which have been acquired by a same kind of modality, display processing can be performed so that the image data in the ROI are superimposed and displayed on the second medical image data which have been acquired in a different period or under imaging conditions for obtaining a different contrast.

On the other hand, when medical image data sets belonging to multiple series have been acquired by different kinds of modalities, multiple frames of the medical image data acquired by the multiple different modalities are acquired in the image acquisition part 10.

Then, the display processing part 11 is configured to perform display processing so that medical image data in a ROI on at least one frame of medical image data which have been acquired by at least one modality out of the multiple modalities are displayed simultaneously with medical image data which have been acquired by another modality. For example, display processing can be performed so that medical image data in a ROI on medical image data which have been acquired by one of the MRI apparatus 3, the X-ray CT apparatus 4 and the PET apparatus 5 are displayed simultaneously with medical image data which have been acquired by another image diagnostic apparatus 6.

Medical image data to be a target of comparative reading may be not only tomographic image data but other 3D (three dimensional) image data. Note that, the 3D image data here means 2D (two dimensional) image data generated for a display, using spatial image data, such as volume image data or multi slice data, as original data.

Concrete examples of 3D image data include volume rendering (VR) image data, surface rendering (SR) image data, multi planar reconstruction (MPR) image data and maximum intensity projection (MIP) image data.

However, depending on a kind of 3D image data, coordinate information may not be attached to the image data. In that case, the display processing part 11 can refer to original data, such as volume image data, used to generate 3D image data, to be a display target, in order to acquire coordinate information of the 3D image data. Alternatively, the display processing part 11 may attach or relate spatial coordinate information with 3D image data, to which coordinate information has not been attached conventionally. In that case, the display processing part 11 can acquire coordinate information, in the body coordinate system, of 3D image data by referring to information attached or related with the 3D image data.

Moreover, as mentioned above, display processing may be performed so that image data in a ROI on the first medical image data are superimposed to be displayed on the second image data of a different object as well as a same object. That is, display processing can be performed for comparative reading using reference medical image data.

Next, an operation and an action of the medical image processing apparatus 1 will be described.

Figure 7:
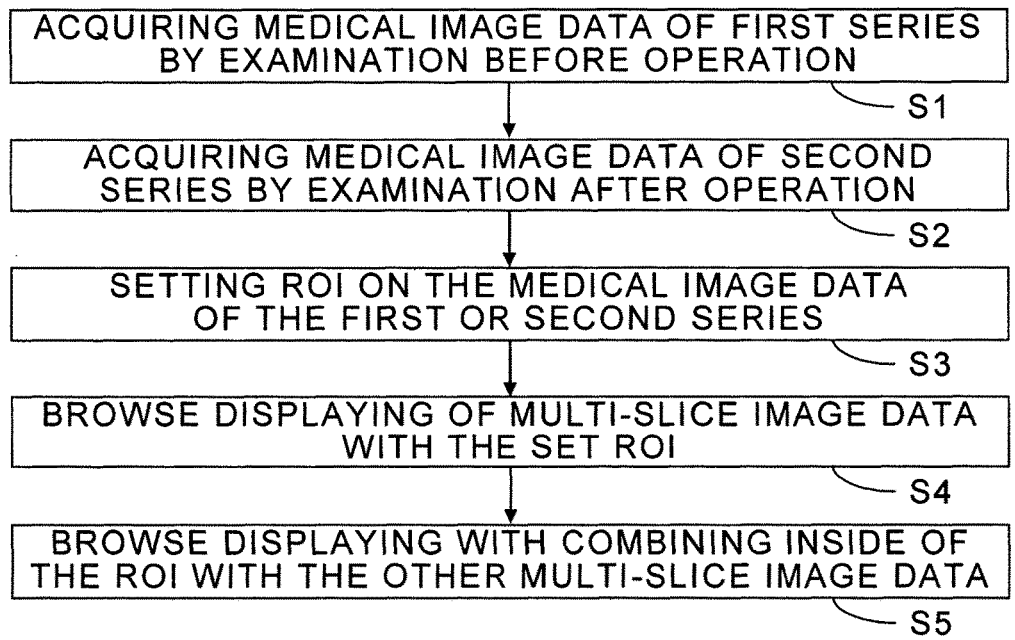
FIG. 7 is a flow chart which shows a flow for displaying medical images for a comparison interpretation in the medical image processing apparatus shown in FIG. 1.

FIG. 7 is a flow chart which shows a flow for displaying medical images for a comparison interpretation in the medical image processing apparatus 1 shown in FIG. 1.

Here, an example case of displaying the first medical image data, acquired for multi slices before an operation, of an object and the second medical image data, acquired for multi slices after the operation, for comparative reading will be described.

First, in Step S1, imaging is performed for a focused region, including a lesion part, before the operation of the object. For example, MR signals are acquired from the object by the imaging system 3A of the MRI apparatus 3, and multi-slice MR image data of the object are generated as the first medical image data. The generated first medical image data can be transferred to the medical image server 7 through the network 2.

Therefore, the first medical image data are controlled and stored as multi-slice image data belonging to the first series in the medical image server 7. On the other hand, a user such as a doctor can perform the operation of the object.

Next, in Step S2, imaging is performed for the focused region including the lesion part after the operation of the object. That is, the second medical image data are acquired in the image diagnostic apparatus 6, such as the MRI apparatus 3, in a flow similar to that for the first medical image data. Thereby, the second medical image data are controlled and stored as multi-slice image data belonging to the second series in the medical image server 7, for example.

Next, in Step S3, a ROI is set to the multi-slice image data belonging to the first series or the multi-slice image data belonging to the second series. The ROI can be set using an arbitrary medical system.

Accordingly, the first medical image data and the second medical image data are taken into the medical image processing apparatus 1 from the medical image server 7, for example. Specifically, the image acquisition part 10 of the medical image processing apparatus 1 acquires the first medical image data and the second medical image data from the medical image server 7 through the network 2 in accordance with an image searching instruction input from the input device 8. The first medical image data and the second medical image data which have been acquired by the image acquisition part 10 are given to the display processing part 11.

Next, setting information of a ROI or ROIs is input from the input device 8. Then, the display processing part 11 sets the ROI or ROIs on the first medical image data or the second medical image data. One ROI can be set for each slice position and each time phase. Moreover, multiple ROIs may be also set on a single frame of slice image data.

Next, in Step S4, a user displays the multi-slice image data, on which the ROI or ROIs have been set, with switching the multi-slice image data in the slice direction, as necessary. Specifically, information for designating a browse direction is input from the input device 8 to the display processing part 11 of the medical image processing apparatus 1. Then, the display processing part 11 sequentially displays the multi-slice image data, on which the ROI or ROIs have been set, before or after the operation, on the display 9 with switching the image data. Thereby, the user can observe a spatial region, including the lesion part, before or after the operation.

Next, in Step S5, the user perform a browse display with combining image data in a ROI or ROIs of the multi-slice image data, on which the ROI or ROIs have been set, with the other multi-slice image data on which no ROI has been set. Specifically, information for selecting multi-slice image data to be a composite target and information for designating a browse direction are input from the input device 8 to the display processing part 11 of the medical image processing apparatus 1, for example. Then, the display processing part 11 performs extraction processing of image data in a ROI or ROIs on the multi slice image data, on which the ROI or ROIs have been set, before or after the operation, for each slice position in order. Subsequently, the extracted image data in the ROI or ROIs at each slice position are combined with the corresponding other multi slice image data.

Then, the display processing part 11 displays the combined multi slice image data with switching them in order. As a result, only an image inside a ROI or images inside ROIs are updated and displayed on the display 9 of the medical image processing apparatus 1 with the state where an image outside the ROI or the ROIs is fixed between the first and the second series. Thereby, the user can observe a spatial region, including the lesion part before and after the operation.

Note that, information for relating extracted medical image data in a ROI or ROIs to medical image data used as a composition destination may be created and attached to at least one of the medical image data in the ROI or the ROIs and the medical image data serving as the composition destination. The processing of creating this link information can also be performed in the display processing part 11. Thereby, when medical image data are displayed again for comparative reading, combined medical image data can be restored quickly. Further, attaching link information to medical image data and transferring the medical image data allow a reproduction of combined medical image data in another medical image processing apparatus.

That is, the medical age processing apparatus 1 described above is an apparatus configured to make medical image data, outside a ROI or ROIs, in common between different series so that a size of medical image data used for comparative reading can be reduced.

For this reason, according to the medical image processing apparatus 1, only a region marked by setting a ROI can be browsed as well as the whole image. Moreover, multiple images which have been imaged in different periods can be observed simultaneously by displaying and superimposing an image in a ROI on a position, different from a corresponding position, of another image.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A medical image processing apparatus comprising:
    at least one data processor coupled with digital storage, an operator input port and an operator display output port, said processor being configured to acquire plural series of image data, each series including frames of medical image data corresponding to at least one of slice positions and time phases; and
    display image data in a region of interest of at least one frame of first medical image data belonging to a first series out of the plural series, the image data in said region of interest being overlapped with a different region of at least one frame of second medical image data belonging to a second series out of the plural series, the different region of the at least one frame of the second medical image data being different from a region corresponding to the region of interest wherein the second medical image data, in which the image data in the region of interest in the first medical image data are overlapped with the region different from the region corresponding to the region of interest are switched and displayed in a slice direction or a time phase direction in the second series at a switching frequency different from a switching frequency of the image data in the region of the interest, the second medical image data being switched and displayed responsive to an instruction for switching the first medical image data in a slice direction or a time phase direction in the first series, the instruction being input from the operator input port.

2. The medical image processing apparatus of claim 1, wherein said processor is configured to perform display processing for switching and displaying the image data in the region of interest, according to a slice position or a time phase of the second medical image data.

3. The medical image processing apparatus of claim 1, wherein said processor is configured to perform display processing for displaying frames of the second medical image data lined up in a slice direction or a time phase direction, and overlapping pieces of image data in regions of interests of frames of the first medical image data at slice positions or time phases corresponding to slice positions or time phases of the frames of the second medical image data, the pieces of the image data being respectively overlapped with regions different from regions, corresponding to the regions of interests, of the frames of the second medical image data.

4. The medical image processing apparatus of claim 1, wherein said processor is configured to perform display processing for overlapping the image data, in the region of interest, with second medical image data of a different object.

5. The medical image processing apparatus of claim 1, wherein said processor is configured to perform display processing for overlapping the image data, in the region of interest, with second medical image data of a same object.

6. The medical image processing apparatus of claim 5, wherein said processor is configured to perform display processing for overlapping the image data, in the region of interest, with second medical image data acquired by a different kind of modality.

7. The medical image processing apparatus of claim 5, wherein said processor is configured to perform display processing for overlapping the image data, in the region of interest, with second medical image data acquired by a same kind of modality.

8. The medical image processing apparatus of claim 7, wherein said processor is configured to perform display processing for overlapping the image data, in the region of interest, with second medical image data acquired at a different time and date.

9. The medical image processing apparatus of claim 7, wherein said processor is configured to perform display processing for overlapping the image data, in the region of interest, with second medical image data acquired using an imaging condition for obtaining a different contrast.

10. The medical image processing apparatus of claim 1, wherein said processor is configured to perform display processing for overlapping the image data, in the region of interest, within a predetermined range, from the region corresponding to the region of the interest, of the second medical image data.

11. The medical image processing apparatus of claim 1, wherein said processor is configured to perform display processing for overlapping the image data, in the region of interest, with a position of the second medical image data, the position being designated using said operator input port or another input port.

12. The medical image processing apparatus of claim 1, wherein said processor is configured to perform enlargement processing or reduction processing of the image data in region of the interest, according to a spatial resolution of the image data in the region of interest.

13. The medical image processing apparatus of claim 1, wherein said processor is configured to perform display processing for overlapping image data, in a corresponding region of interest of at least one frame of third medical image data belonging to a third series out of the plural series, on a position different from each of a corresponding region of the second medical image data and a position of the image data in the region of interest of the at least one frame of the first medical image data.

14. A magnetic resonance imaging apparatus comprising:
an imaging system configured to acquire plural series of image data, each series including frames of medical image data corresponding to at least one of slice positions and time phases, by magnetic resonance imaging; and
at least one data processor provided with digital storage an operator input port and an operator display output port, said processor being configured to perform display processing to display image data in a region of interest of at least one frame of first medical image data belonging to a first series out of the plural series, the image data in the region of interest being overlapped with a different region of at least one frame of second medical image data belonging to a second series out of the plural series, the different region of the at least one frame of the second medical image data being different from a region corresponding to the region of interest wherein the second medical image data, in which the image data in the region of interest in the first medical image data are overlapped with the region different from the region corresponding to the region of interest are switched and displayed in a slice direction or a time phase direction in the second series at a switching frequency different from a switching frequency of the image data in the region of the interest, the second medical image data being switched and displayed responsive to an instruction for switching the first medical image data in a slice direction or a time phase direction in the first series, the instruction being input from the operator input port.

15. A medical image processing method comprising:
configuring and
using a data processor provided with digital storage, an operator input port and an operator display output port to effect
acquiring plural series of image data, each series including frames of medical image data corresponding to at least one of slice positions and time phases; and
performing display processing to display image data in a region of interest of at least one frame of first medical image data belonging to a first series out of the plural series, the image data in the region of interest being overlapped with a different region of at least one frame of second medical image data belonging to a second series of the plural series, the region of the at least one frame of the second medical image data being different from a region corresponding to the region of interest wherein the second medical image data, in which the image data in the region of interest in the first medical image data are overlapped with the region different from the region corresponding to the region of interest are switched and displayed in a slice direction ora time phase direction in the second series at a switching frequency different from a switching frequency of the image data in the region of the interest, the second medical image data being switched and displayed responsive to an instruction for switching the first medical image data in a slice direction or a time phase direction in the first series, the instruction being input from the operator input port.

16. A magnetic resonance imaging (MRI) method comprising:
Using an MRI system to acquire plural series of image data, each series including frames of medical image data corresponding to at least one of slice positions and time phases, by magnetic resonance imaging; and using at least one data processor to perform display processing to display image data in a region of interest of at least one frame of first medical image data belonging to a first series out of the plural series, the image data in the region of interest being overlapped with a different region of at least one frame of second medical image data belonging to another series, the different region of the at least one frame of the second medical image data being different from a region corresponding to the region of interest wherein the second medical image data, in which the image data in the region of interest in the first medical image data are overlapped with the region different from the region corresponding to the region of interest are switched and displayed in a slice direction or a time phase direction in the second series at a switching frequency different from a switching frequency of the image data in the region of the interest, the second medical image data being switched and displayed responsive to an instruction for switching the first medical image data in a slice direction or a time phase direction in the first series, the instruction being input from the operator input port.

* * * * *